(12) United States Patent
Lee

(10) Patent No.: US 6,255,556 B1
(45) Date of Patent: Jul. 3, 2001

(54) LEAN TRANSGENIC ANIMALS

(75) Inventor: Ying-Hue Lee, Santrung (TW)

(73) Assignee: Academia Sinica (TW)

( * ) Notice: Subject to any disclaimer, the term of this patent is extended or adjusted under 35 U.S.C. 154(b) by 0 days.

(21) Appl. No.: 09/500,841

(22) Filed: Feb. 10, 2000

(51) Int. Cl.$^7$ .................. G01N 33/00; G01K 67/027; C12N 15/00

(52) U.S. Cl. .................. 800/18; 800/3; 800/21; 435/320.1

(58) Field of Search .................. 800/3, 13, 18, 800/21; 435/320.1

(56) References Cited

PUBLICATIONS

Wall, Theriogenology, 1996, 45:57–68.*
Ebert, et al., 1988, Molecular Endocrinology, 2:277–83.*
Mullins, et al., 1996, 98(11):S37–S40.*
Freytag, 1994, Genes and Development, 8:1654–63.*
Cowherd et al., "Molecular regulation of adipocyte differentiation," Cell & Developmental Biology, vol. 10, pp. 3–10, 1999.
Fajas et al., "Transcriptional control of adipogenesis," Current Opinion in Cell Biology, vol. 10, pp. 165–173, 1998.
Spiegelman et al., "Adipogenesis and Obesity: Rounding Out the Big Picture," Cell, vol. 87, pp. 277–389, 1996.
Wang et al., "Impaired Energy Homeostasis in C/EBPα Knockout Mice," Science, vol. 269, pp. 1108–1112, 1995.
Lee et al., "Disruption of the c/ebpα Gene in Adult Mouse Liver," Molecular and Cellular Biology, vol. 17, pp. 6014–6022, 1997.

* cited by examiner

Primary Examiner—Deborah J. R. Clark
Assistant Examiner—Eleanor Sorbello
(74) Attorney, Agent, or Firm—Fish & Richardson P.C.

(57) ABSTRACT

The invention relates to a transgenic animal whose genomic DNA includes a gene comprising a C/EBPα promoter operably linked to a DNA sequence encoding a C/EBPβ polypeptide, wherein the transgenic animal exhibits reduced accumulation of fat in its white adipose tissue, as compared to a reference animal whose genomic DNA does not contain the gene.

12 Claims, No Drawings

LEAN TRANSGENIC ANIMALS

BACKGROUND OF THE INVENTION

Obesity is a significant risk factor for many serious illnesses, such as heart disease, arthritis, and diabetes. To better understand the mechanisms that lead to obesity and to develop strategies to control certain types of obesity, a better knowledge of the molecular events that regulate fat cell differentiation and fat storage is needed at the organismal level. Transgenic animals with altered fat metabolism provide a unique opportunity to probe the relationships between gene expression and fat metabolism.

SUMMARY OF THE INVENTION

The invention is based on a new transgenic animal that contains a CCAAT/enhancer-binding protein (C/EBP) α gene in which the open reading frame encoding the C/EBPα polypeptide has been replaced with a C/EBPβ open reading frame. This animal exhibits decreased accumulation of fat in white adipose tissue (WAT). Thus, the transgenic animals of the invention offers a unique animal model in which the genetic and biochemical mechanisms responsible for decreased WAT mass can be deciphered.

Accordingly, the invention features a transgenic animal (e.g., a non-human mammal, rodent, rat, mouse, rabbit, pig, cow, chicken, or fish) whose genomic DNA includes a gene having a C/EBPα promoter operably linked to a DNA sequence encoding a C/EBPβ polypeptide. By "operably linked" is meant that a nucleotide sequence (e.g., an open reading frame) is linked to a regulatory sequence (e.g., a promoter) in a manner which allows for expression of the nucleotide sequence in vitro or in vivo. The transgenic animal exhibits reduced accumulation of (e.g., a statistically significant reduction in) fat in its WAT, as compared to a reference animal (e.g., the wild-type animal from which the transgenic animal was generated) whose genomic DNA does not contain the gene.

A "C/EBPα" promoter refers to a promoter that directs transcription of an RNA in a temporal and cell-type specific manner at least substantially similar, if not identical, to the expression of a wild-type C/EBPα gene. Thus, a "C/EBPα" promoter includes wild-type C/EBPα promoters as well as such promoters containing insertions, deletions, or substitutions that do not affect the temporal and tissue-specific expression of the C/EBPα promoter. Similarly, a "C/EBPβ polypeptide" is a polypeptide that has at least one biochemical or cellular activity associated with a wild-type C/EBPβ polypeptide. Thus, a C/EBPβ polypeptide includes wild-type C/EBPβ polypeptides as well as such polypeptides containing amino acid insertions, deletions, or substitutions that do not affect the biochemical or cellular activity of the C/EBPβ polypeptide.

The genomic DNA of the transgenic animal can also contain multiple copies (i.e., two or more copies) of the gene, so long as the transgenic animal exhibits reduced accumulation of fat in its white adipose tissue. In addition, when the gene is made by replacing a portion of a wild-type endogenous C/EBPα gene with a C/EBPβ open reading frame, the transgenic animal can be homozygous or heterozygous for the mutated C/EBPα gene.

The transgenic animal of the invention can also include one or more of the following phenotypes: the size of adipocytes in the WAT of the transgenic animal is smaller than the size of adipocytes in the WAT of the reference animal; the serum glucose and triacylglyceride levels in the transgenic animal are substantially the same (i.e., with no statistically significant difference) as those in the reference animal; the transgenic animal consumes more food than the reference animal, provided that the amount of food available is not limiting and the same type of food is presented to the transgenic and reference animals; reduced accumulation of fat is observed when the transgenic and reference animals are fed a diet that is at least about 30% by weight fat; the expression level of adipsin in the white adipose tissue of the transgenic animal is reduced as compared to the expression level of adipsin in the white adipose tissue of the reference animal; the expression level of leptin in the white adipose tissue of the transgenic animal is reduced as compared to the expression level of leptin in the white adipose tissue of the reference animal; the total mass of brown adipose tissue in the transgenic animal is greater than the total mass of brown adipose tissue in the reference animal; and the mitochondrial content in the white adipose tissue of the transgenic animal is greater than the mitochondrial content in the white adipose tissue of the reference animal. The terms "smaller," "reduced," "more," or "greater" can refer to differences that are statistically significant.

The invention also features a method of producing a transgenic animal of the invention by replacing at least a portion of a C/EBPα gene in the genomic DNA of the transgenic animal with a DNA insert comprising a first sequence encoding a C/EBPβ polypeptide and a second sequence encoding a selectable marker; and removing the second sequence from the genomic DNA, thereby producing the transgenic animal.

In addition, the invention includes a nucleic acid comprising a C/EBPα promoter operably linked to a sequence encoding C/EBPβ polypeptide, which is useful for producing a transgenic animal of the invention.

The transgenic animals of the invention can be used to elucidate the biochemical and genetic determinants that provide for a lean (low fat) body. For example, cDNA from white adipose tissue of the transgenic and reference animal can be interrogated with DNA chips to uncover any differences in expression profiles. Individual hits, or genes showing significant changes in expression, may be or encode for potential drugs or drug targets for decreasing body fat.

Other features or advantages of the present invention will be apparent from the following detailed description and also from the claims.

DETAILED DESCRIPTION

The invention relates to transgenic animals that exhibit reduced white adipose tissue. These animals serve as important animal models for elucidating the molecular parameters involved in fat metabolism.

Introduction of a transgene into the fertilized egg of an animal (e.g., a mammal) is accomplished by any number of standard techniques in transgenic technology. See, e.g., Hogan et al., Manipulating the Mouse Embryo: A Laboratory Manual, Cold Spring Harbor Laboratory Press, Cold Spring Harbor, N.Y., 1986; and U.S. Pat. No. 5,811,634. Most commonly, the transgene is introduced into the embryo by way of microinjection.

Once the transgene is introduced into the egg, the egg is incubated for a short period of time and is then transferred into a pseudopregnant animal of the same species from which the egg was obtained (Hogan et al., supra). In the case of mammals, typically 125 eggs are injected per experiment, approximately two-thirds of which will survive the procedure. Twenty viable eggs are transferred into pseudopregnant mammal, four to ten of which will develop into live progeny. Typically, 10–30% of the progeny (in the case of mice) carry the transgene.

To identify the transgenic animals of the invention, progeny are examined for the presence of the transgene using standard procedures such as Southern blot hybridization or PCR. Expression of the transgene can also be assessed using Northern blots, Western blots, and immunological assays.

Without further elaboration, it is believed that one skilled in the art can, based on the above disclosure and the description below, utilize the present invention to its fullest extent. The following example is to be construed as merely illustrative of how one skilled in the art can practice the invention and are not limitative of the remainder of the disclosure in any way. All publications cited in this disclosure are hereby incorporated by reference.

Materials and Methods

Production of Targeting Construct. The C/ebpα genomic fragment used for preparing gene targeting construct was described in Lee et al., Mol. Cell Biol. 17:6014–6022, 1997. In this targeting construct, the entire protein coding region of C/EBPα, (1188 bp, from the start to stop codons), was deleted and replaced with the 831 bp DNA fragment containing the mouse C/EBPβ protein coding region. The loxP-PGK.neo-loxP expression cassette was then inserted into an Spe I site 159 bp downstream of the stop codon TAG. The targeting vector contained 4.1 kb of homologous DNA upstream of the C/EBPα start codon and 3.8 kb of homologous DNA downstream of the loxP-PGK-neo-loxP cassette.

Production of Homozygous Mice. ES cells (RW4, Genome Systems) were electroporated with the linearized targeting vector DNA. G418-resistant clones were selected, expanded, and analyzed by Southern blotting with a 5' probe and a coding region probe to identify specific homologous recombinants. The correctly targeted ES cells were injected into C57BL/6J blastocysts to generate chimeric founder mice as described previously in Hogan et al., Manipulating the mouse embryo: a laboratory manual, 2nd ed., Cold Spring Harbor Laboratory Press, Cold Spring Harbor, N.Y., 1994. Chimeric male founders with close to 90 to 100% agouti coat color were bred with C57BL/6J females. Offspring mice having germ line transmission of the mutant allele were bred with homozygous EIIa-cre mice (Lasko et al., Proc. Natl. Acad. Sci. USA 93:5860–5865, 1996) to remove the targeting marker PGKneo gene from the mouse genome as described in Lee et al., supra. F1 Mice carrying one mutant C/ebpα allele, termed C/ebpαβ, were interbred to generate homozygous C/ebpαβ$^{+/+}$ mice, which had the open reading frame of the endogenous C/EBPα genes replaced with the open reading frame for C/EBPβ.

Southern blot analysis. Isolated ES cell DNA or mouse tail DNA was digested with the appropriate restriction enzyme, electrophoresed in a 0.5% agarose gel, transferred to a nylon membrane (GeneScreen Plus, Dupont) and hybridized with a probes derived from the C/ebpα or C/ebpβ gene.

High Fat (HF) Diet Experiments. All mice used in this study were F3 siblings derived from interbreeding the F2 C/ebpαβ$^{+/-}$ mice. Mice were kept in a sterile microisolator and were observed closely throughout the experiment. For measuring the effect of a HF diet, three mice of each sex and of either genotype were placed separately in microisolator 2.5 weeks after birth. Fresh food of regular (10% fat) or high fat diet (30% fat, LabDiet, Richmond, Id.) was provided daily and the amount of food consumed was recorded daily. To measure their growth rate, mice were monitored for their body weight twice every week.

Histological Analysis of Liver and Adipose Tissues. Epididymal fat pads and livers were fixed in 4% PBS-buffered paraformaldehyde solution for embedding in paraffin or were embedded immediately in tissue freezing medium (OCT, Tissue-Trek, Miles Inc.) and frozen in liquid nitrogen. Sections of 5 μm (for paraffin-embedded tissues) or 10 μm (for frozen tissues) were cut and mounted on silanized slides. The frozen tissue sections were stained with Oil Red O and counter stained with hematoxylin as described Van Goor et al., Histochemistry 85:251–253, 1986. The paraffin tissue sections were stained with hematoxylin and eosin solutions (H&E-staining).

Analyses of Serum Chemistries and levels of Leptin and Insulin. Mouse serum taken from various developmental stages was analyzed in an auto-dry chemical analyzer (SP4410; Spotchem) to monitor levels of serum glucose, triacylglyceride and other blood chemistries. Serum leptin and insulin were assayed with appropriate ELISA kits (Crystal Chem Inc., Chicago, Ill.).

Hemolytic Assay. Serum factor D activity was monitored by a hemolytic assay using rabbit erythrocytes and factor-D-depleted human serum as described in Biochem. J. 279:775–779, 1991. In a total assay volume of 150 μl, 25 μl of mouse serum and 25 μl of factor-D-depleted human serum were added to rabbit erythrocytes ($10^7$ cells in 100 μl of 5 mM Veronal-buffered saline, 12 mM $MgCl_2$, pH 7.4). After incubation at 37° C. for one hour, the hemolytic activity was determined, and the activity was expressed as a percentage of that in a lysed control.

RNA Extraction and Northern Bolt Analysis. Frozen mouse tissues were homogenized in TRIzol RNA reagent (GIBCO-BRL), and total RNA were isolated according to the manufacturer's protocol. Total RNA (10 μg) was denatured, electrophoresed, transferred to a nylon membrane, and probed with cDNA probes by using standard protocols.

Mitochondrial DNA Isolation. Nuclei and mitochondria of epididymal fat pads were isolated and their DNA were extracted as described in Plava et al., FEBS 192:267–270, 1985. The extracted nuclear DNA and mitochondrial DNA were further treated with proteinase K and DNase-free RNase at the final concentration of 100 μg/ml for each. DNA was then precipitated with isopropanol twice before resuspension in 10 mM Tris-HCl, pH 8.0, 1 mM EDTA. DNA was quantified by measuring absorbency at 260 nm and 280 nm in an UV spectrometer.

Results

The C/EBPβ knockin targeting vector was constructed to replace the entire protein coding region of C/EBPα with that of C/EBPβ in the C/ebpα gene locus. A loxP-PGK.neo-loxP cassette was inserted downstream of the stop codon to serve as the targeting selection marker. Cre-mediated recombination would result in removal of the marker gene from the C/ebpα gene locus. After transfection of the linearized targeting vector DNA into ES cells, 1% of the G418-resistant ES clones were found to carry a mutant C/ebpα allele in which the protein coding region of C/EBPα was deleted and replaced with that of C/EBPβ. Mice having germ line transmission of the mutant allele, termed C/ebpαβ, were produced. The C/ebpαβ$^{+/-}$ mice were interbred to generate homozygous C/ebpαβ$^{+/+}$ mice. Deletion of the C/EBPα protein coding region in the manipulated C/ebpα gene locus was confirmed by Southern analysis with a 1.2 kb DNA probe (Probe I) containing the entire protein coding region and a 2 kb probe (Probe II) covering the full length C/EBPα transcript. In addition, presence of the C/EBPβ protein coding region in the C/ebpα gene locus was confirmed by probing the C/ebpαβ$^{+/+}$ mouse genome with a C/EBPβ cDNA probe (Probe III). Furthermore, to eliminate the potential interference on the C/EBPαβ expression by the PGK.neo marker gene, which was introduced into the C/ebpα gene locus during the targeting steps, C/ebpαβ$^{+/+}$ mice were then bred with a cre transgenic mouse line to remove the PGK.neo marker gene from the C/ebpαβ locus according to Lee et al., supra, and Lasko et al., supra. The resulting F1 mice heterozygous for the C/ebαβ allele and lacking the marker gene were selected for interbreeding to yield F2 C/ebpαβ$^{+/+}$ mice. The absence of C/EBPα mRNA expression and the presence of the C/EBPαβ mRNA (1.8 kb) in C/ebpαβ$^{+/+}$ mice were further confirmed by probing total RNAs extracted from various tissues, such as liver and fat tissues, with the respective cDNA probes.

Reduced Fat storage in White Adipose Tissues of C/ebpαβ$^{+/+}$ Mice. The C/EBPα null mice died shortly after birth, possibly due to lack of glycogen storage and a severe hypoglycemia at birth. On the other hand, the newborns of C/ebpαβ$^{+/+}$ mice were viable and had blood glucose levels similar to those of wild-type littermates. The mice exhibited no detectable abnormality in their appearance at birth and during the period of this study. In addition, the C/ebpαβ$^{+/+}$ mice did not differ from their wild-type littermates in their growth rate, as measured by body weight gain. Both sexes of C/ebpαβ$^{+/+}$ mice were fertile. However, the average time required for female C/ebpαβ$^{+/+}$ mice to deliver the first litter of pups was 2 weeks longer than those for the wild-type and C/ebpαβ$^{+/-}$ female littermates. In spite of the delay in pregnancy, C/ebpαβ$^{+/+}$ female mice had normal pregnant frequency afterward as did their wild-type littermates during the period of this study.

Despite the similar body weights between C/ebpαβ$^{+/+}$ and wild-type mice, C/ebpαβ$^{+/+}$ mice differed strikingly from wild-type mice in size and appearance of their WAT. WAT in C/ebpαβ$^{+/+}$ mice could be located in the respective areas based on the distribution profile in wild-type mice. However, WAT masses in C/ebpαβ$^{+/+}$ mice appeared small and yellowish, whereas those in wild-type littermates were significantly enlarged and appeared whitish. Histological section and Oil-Red O staining indicated that the size of adipocyte and the degree of lipid accumulation were markedly reduced in WAT of C/ebpαβ$^{+/+}$ mice. On the other hand, serum glucose and triacylglyceride levels were not reduced in C/ebpαβ$^{+/+}$ mice. These results suggested that the lipid accumulation in WAT of C/ebpαβ$^{+/+}$ mice was inhibited, and that this inhibition was not due to lack of lipid precursors in circulation. WAT of C/ebpαβ$^{+/+}$ mice at the age of 10 weeks or older were larger and had more fat storage, but they were significantly smaller than those of wild-type mice of the same age.

Resistance of High Fat (HF) Diet-Induced Adipocyte Hypertrophy in C/ebpαβ$^{+/+}$ mice. C/ebpαβ$^{+/+}$ mice were lean but had a normal growth rate. Surprisingly, measurement of the food intake revealed that C/ebpαβ$^{+/+}$ mice consumed more food than their wild-type littermates. To determine whether the food content would affect the status of fat storage in WAT of C/ebpαβ$^{+/+}$ mice, C/ebpαβ$^{+/+}$ mice were kept under a HF diet (30% fat) for 6 weeks. Food consumption, body weight gain, and WAT mass of C/ebpαβ$^{+/+}$ male mice were monitored during dieting. Under the HF diet, C/ebpαβ$^{+/+}$ mice consumed more food than wild-type mice did throughout the 6-week period. However, body weight gain for C/ebpαβ$^{+/+}$ male mice under the HF diet did not differ from that for C/ebpαβ$^{+/+}$ male mice under the standard diet. By contrast, the body weight for wild-type male mice under the HF diet was 25% heavier than that under the standard diet. In addition, WAT mass in wild-type male mice under the HF diet was 3 fold higher than that in mice under standard diet, whereas fat masses did not differ significantly between C/ebpαβ$^{+/+}$ male mice under either diet. These results indicated that C/ebpαβ$^{+/+}$ male mice resisted WAT mass increases under the HF diet.

Reduced Expressions of Leptin and Adipsin in Adipose Tissues of C/ebpαβ$^{+/+}$ Mice. To understand the molecular mechanism underlying the resistance of fat accumulation in WAT of C/ebpαβ$^{+/+}$ mice, expression of numerous genes whose function are related to the adipocyte differentiation and maturation was first examined. The mRNA levels of C/EBPβ expressed from its endogenous gene locus (as a 1.5 kb transcript) appeared to be up regulated in WAT of C/ebpαβ$^{+/+}$ mice. The levels of C/EBPβ expressed from the C/ebpα gene locus (as a 1.8 kb transcript) were similar to those from the C/EBPβ gene locus. mRNA Levels of other transcription regulators involved in adipocyte development, such as peroxisome proliferator activated receptor (PPARγ) and adipocyte determination and differentiation-dependent factor (ADD1/SREBP-1), were not different in WAT between C/ebpαβ$^{+/+}$ and wild-type mice. Similarly, aP2 and glucose transporter IV (GLUT4), which are expressed in mature adipocytes, were not affected in WAT of C/ebpαβ$^{+/+}$ mice. Expression of enzymes involved in fatty acid synthesis, such as fatty acid synthetase (FAS) and stearyl-CoA-desaturase (SCD), were not significantly different between wild-type and C/ebpαβ$^{+/+}$ mice. These results indicated that the expression of the above factors, which all play a role in adipogenesis, were not inhibited in WAT of C/ebpαβ$^{+/+}$ mice. However, mRNA levels encoding two factors expressed specifically in mature adipocytes, adipsin (Factor D) and leptin (product of ob gene), were significantly reduced in WAT of C/ebpαβ$^{+/+}$ mice.

Adipsin and leptin are produced in WAT, released into circulation, and involved in maintaining energy homeostasis, particular in regulating lipid storage in WAT. To determine whether the adipsin levels in blood of C/ebpαβ$^{+/+}$ were reduced to reflect their mRNA levels in WAT, a hemolysis assay was carried out to determine the adipsin activity in serum of C/ebpαβ$^{+/+}$ mice. Indeed, haemolytic activity in serum of C/ebpαβ$^{+/+}$ mice was reduced to 50% of that in serum of wild-type mice. Similarly, serum leptin levels in C/ebpαβ$^{+/+}$ mice were significantly reduced.

Increased Mitochondrial Content and Energy Oxidation in WAT of C/ebpαβ$^{+/+}$ mice. Adipsin is a serine protease involved in generating the active complement C3a (also known as acylation stimulating protein (ASP) 12). ASP stimulates triglyceride synthesis in adipocytes. The reduction in adipsin levels in the circulation of C/ebpαβ$^{+/+}$ mice suggested that the signaling for fat storage in adipocytes was defective, which might explain in part the reduction of fat storage in WAT of C/ebpαβ$^{+/+}$ mice. However, under a HF diet, C/ebpαβ$^{+/+}$ mice, in spite of consuming more food, were also resistant to the HF diet-induced adipocyte hypertrophy as seen in wild-type mice. Moreover, despite the markedly reduced fat storage in their WAT, C/ebpαβ$^{+/+}$ mice did not developed hyperlipidemia. Similarly, histological analysis of liver did not detect fatty liver in C/ebpαβ$^{+/+}$ mice. Therefore, it raised the prevention of fat accumulation in WAT and liver of C/ebpαβ$^{+/+}$ mice might involve other mechanisms, such as an increase in energy expenditure.

To determine the status of energy expenditure in C/ebpαβ$^{+/+}$ mice, we first measured body temperature and brown adipose tissue (BAT) mass of C/ebpαβ$^{+/+}$ mice. The body temperature of C/ebpαβ$^{+/+}$ mice (29.1±0.3° C.) was 0.5 to 0.7° C. higher than that of their wild-type littermates (28.5±0.2° C.), indicating that C/ebpαβ$^{+/+}$ mice have higher energy expenditures. BAT is a major tissue for thermogenesis; it is designed not to store but to release energy as heat through a very high activity for uncoupled oxidation of fatty acid. Unlike their WAT, C/ebpαβ$^{+/+}$ mice had 65% higher BAT mass than wild-type mice. In addition, adipocytes in BAT of C/ebpαβ$^{+/+}$ mice were highly vacuolate. However, the mRNA levels of uncoupling protein (UCP1) and cytochrome b, which are involved in thermogenesis and the mitochondria electron transfer system for oxidation, respectively, were not different in BAT between wild-type and C/ebpαβ$^{+/+}$ mice, suggesting that the metabolic activity of BAT was not affected in C/ebpαβ$^{+/+}$ mice. These results indicated that the higher energy expenditure in C/ebpαβ$^{+/+}$ mice might not solely depend on the uncoupled oxidation in BAT. Whether the oxidation activity of other tissues was altered in C/ebpαβ$^{+/+}$ mice was therefore examined by probing total RNA isolated from various tissues with probes for mitochondrial genes encoding enzymes for the electron transfer chain.

mRNA levels of both mitochondrial cytochrome b and NADH dehydrogenase were markedly increased in WAT of C/ebpαβ$^{+/+}$ mice compared to the levels in wildtype mice, and this increase was specific in WAT. To examine whether the increase of mitochondria mRNA for electron transfer system is due to an increase of cellular mitochondria number, we isolated and quantified mitochondria from epididymal WAT of C/ebpαβ$^{+/+}$ mice by measuring their DNA content. Indeed, C/ebpαβ$^{+/+}$ mice harbored 52% more mitochondria than wild-type mice in adipocytes of their epididymal WAT, indicating that the WAT of C/ebpαβ$^{+/+}$ mice possesses higher oxidation capability than that of wild-type mice.

Interestingly, however, BAT oxidative activity, in terms of UCP1 expression, was not elevated in C/ebpαβ$^{+/+}$ mice which lacked C/ebpαβ$^{+/+}$ but have a concomitant gain of C/EBPβ. By contrast, mRNA levels of UCP1 were significantly higher in WAT of C/ebpαβ$^{+/+}$ mice compared to levels in wild-type mice. Increased mitochondria content and elevated UCP1 expression suggested that WAT of C/ebpαβ$^{+/+}$ mice acquired higher metabolic activity and uncoupled oxidation, a status reminiscent of energy metabolism in BAT. Thus, the prevention of fat accumulation in WAT of C/ebpαβ$^{+/+}$ mice may involve both reduced production of stimulators for lipid storage and an elevated oxidative activity in WAT itself.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

For example, a C/EBPβ open reading frame and a C/EBPα promoter that drives its expression can be delivered by a viral (e.g., retroviral vector) in a gene therapy method in animals in which a reduction in WAT is desired. In addition, while the replacement of an open reading frame in an endogenous C/EBPα is described above, neither the C/EBPβ open reading frame nor the C/EBPα promoter that drives its expression need to correspond with any endogenous sequences of the animal.

What is claimed is:

1. A transgenic mouse whose genomic DNA comprises a gene comprising an introduced DNA sequence encoding a naturally occurring mouse C/EBPβ polypeptide, the introduced DNA sequence replacing an endogenous sequence encoding at least a portion of an C/EBPα polypeptide; and an endogenous mouse C/EBPα promoter operably linked to the introduced DNA sequence, wherein the transgenic mouse exhibits reduced accumulation of fat in its white adipose tissue, as compared to a reference mouse whose genomic DNA does not contain the gene.

2. The transgenic mouse of claim 1, whose genomic DNA comprises two copies of the gene.

3. The transgenic mouse of claim 1, wherein the size of adipocytes in the white adipose tissue of the transgenic mouse is smaller than the size of adipocytes in the white adipose tissue of the reference mouse.

4. The transgenic mouse of claim 1, wherein the serum glucose and triacylglyceride levels in the transgenic mouse are about the same as those in the reference mouse.

5. The transgenic mouse of claim 1, wherein the transgenic mouse consumes more food than the reference mouse, provided that the amount of food available is not limiting and the same type of food is presented to the transgenic and reference mice.

6. The transgenic mouse of claim 1, wherein the reduced accumulation of fat is observed when the transgenic and reference mice are fed a diet comprising about 30% by weight fat.

7. The transgenic mouse of claim 1, wherein the expression level of adipsin in the white adipose tissue of the transgenic mouse is reduced as compared to the expression level of adipsin in the white adipose tissue of the reference mouse.

8. The transgenic mouse of claim 1, wherein the expression level of leptin in the white adipose tissue of the transgenic mouse is reduced as compared to the expression level of leptin in the white adipose tissue of the reference mouse.

9. The transgenic mouse of claim 1, wherein the total mass of brown adipose tissue in the transgenic mouse is greater than the total mass of brown adipose tissue in the reference mouse.

10. The transgenic mouse of claim 1, wherein the mitochondrial content in the white adipose tissue of the transgenic mouse is greater than the mitochondrial content in the white adipose tissue of the reference mouse.

11. The transgenic mouse of claim 1, wherein the size of adipocytes in the white adipose tissue of the transgenic mouse is smaller than the size of adipocytes in the white adipose tissue of the reference mouse;

the serum glucose and triacylglyceride levels in the transgenic mouse are about the same as those in the reference mouse;

the transgenic mouse consumes more food than the reference mouse, provided that the amount of food available is not limiting and the same type of food is presented to the transgenic and reference mice;

the reduced accumulation of fat is observed when the transgenic and reference mice are fed a diet comprising about 30% by weight fat;

the expression level of adipsin in the white adipose tissue of the transgenic mouse is reduced as compared to the expression level of adipsin in the white adipose tissue of the reference mouse;

the expression level of leptin in the white adipose tissue of the transgenic mouse is reduced as compared to the expression level of leptin in the white adipose tissue of the reference mouse;

the total mass of brown adipose tissue in the transgenic mouse is greater than the total mass of brown adipose tissue in the reference mouse; and the mitochondrial content in the white adipose tissue of the transgenic mouse is greater than the mitochondrial content in the white adipose tissue of the reference mouse.

12. A method of producing a transgenic mouse, wherein said method comprises:
  a) introducing an exogenous DNA construct comprising a nucleotide sequence which encodes a mouse C/EBPβ protein and a nucleotide sequence encoding a selectable marker, into a mouse ES cell wherein said exogenous DNA construct replaces at least part of the endogenous C/EBPα encoding sequences and results in an operable linkage between the C/EBPβ coding sequence and the C/EBPα promoter;
  b) injecting the mouse ES cell into a blastocyst and transplanting said blastocyst into the oviduct of a mouse;
  c) allowing said blastocyst to develop into a mouse whose genome contains said exogenous DNA construct;
  d) breeding said mouse to remove the selectable marker and produce homozygous offspring; and
  e) screening said progeny to identify a transgenic mouse whose genome comprises an ORF of the exogenous C/EBPβ gene;
  wherein said progeny exhibits a reduced accumulation of fat in its white adipose tissue as compared to a mouse without said exogenous C/EBPβ gene in its genome.

* * * * *